(12) United States Patent
Ishino et al.

(10) Patent No.: US 7,211,647 B2
(45) Date of Patent: May 1, 2007

(54) DNA SYNTHETASE

(75) Inventors: Yoshizumi Ishino, Fukuoka (JP); Isaac Cann, Savoy, IL (US); Arnaud Bocquier, Quebec (CA); Lidong Liu, Seattle, WA (US)

(73) Assignee: Celestar Lexico-Sciences, Inc., Chiba (JP)

( * ) Notice: Subject to any disclaimer, the term of this patent is extended or adjusted under 35 U.S.C. 154(b) by 172 days.

(21) Appl. No.: 10/343,049

(22) PCT Filed: Jul. 27, 2001

(86) PCT No.: PCT/JP01/06465

§ 371 (c)(1),
(2), (4) Date: Jul. 14, 2003

(87) PCT Pub. No.: WO02/10360

PCT Pub. Date: Feb. 7, 2002

(65) Prior Publication Data

US 2004/0014072 A1 Jan. 22, 2004

(30) Foreign Application Priority Data

Jul. 28, 2000 (JP) .............................. 2000-229382

(51) Int. Cl.
*C07K 14/195* (2006.01)
(52) U.S. Cl. .................... 530/350; 530/395; 530/820; 530/825; 435/69.1
(58) Field of Classification Search ................ 530/350, 530/395, 820, 825; 435/69.1
See application file for complete search history.

(56) References Cited

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Bocquier et al. (Current Biology, Mar. 20, 2001, vol. 11, pp. 452-456).*
Augustin et al. (Nature Structural Biology, Jan. 2001, vol. 8 No. 1, pp. 57-61).*
STIC search report on SEQ ID No. 1.*
Desogus et al, *Nucleic Acids Research*, 27:4444-4450 (1999).
Augustin et al, *Nature Structural Biology*, 8:57-61 (2001).
Bocquier et al, *Current Biology*, 11(6):452-456 (2001).
Goulian et al, *J. of Biol. Chem.*, 265(22):13221-13230 (1990).
Bialek et al, *Embo J.*, 8(6):1833-1839 (1989).
Tseng et al, *Biochemistry*, 39(7):1646-1654 (2000).
Kawarabayashi et al, *DNA Res.*, 5(2):55-76 (1998).

* cited by examiner

*Primary Examiner*—Robert A. Zeman
(74) *Attorney, Agent, or Firm*—Sughrue Mion, PLLC

(57) ABSTRACT

The object of the invention is to provide proteins that have both DNA primase activity and DNA polymerase activity. This subject is solved by a protein (p41) that has an amino acid sequence shown in SEQ ID NO: 1. This is for the first time that proteins that have both DNA primase activity and DNA polymerase activity were found. A protein (p46) that has amino acid sequence shown in SEQ ID NO: 2 forms a complex with p41, and enforces DNA synthesis activity that is independent and/or dependent from primer of p41.

3 Claims, 7 Drawing Sheets

1. p41 (2μl)
2. p41 + p46
3. p41 – p46 Complex
4. p41 (8μl)

SEQUENCE LISTING

```
<160> NUMBER OF SEQ ID NOS: 9

<210> SEQ ID NO 1
<211> LENGTH: 347
<212> TYPE: PRT
<213> ORGANISM: Pyrococcus furiosus

<400> SEQUENCE: 1

Met Leu Met Arg Glu Val Thr Lys Glu Glu Arg Ser Glu Phe Tyr Ser
1               5                   10                  15
```

-continued

```
Lys Glu Trp Ser Ala Lys Lys Ile Pro Lys Phe Ile Val Asp Thr Leu
            20                  25                  30

Glu Ser Arg Glu Phe Gly Phe Asp His Asn Gly Glu Gly Pro Ser Asp
        35                  40                  45

Arg Lys Asn Gln Tyr Ser Asp Ile Arg Asp Leu Glu Asp Tyr Ile Arg
    50                  55                  60

Ala Thr Ser Pro Tyr Ala Val Tyr Ser Val Ala Phe Tyr Glu Asn
65                  70                  75                  80

Pro Arg Glu Met Glu Gly Trp Arg Gly Ala Glu Leu Val Phe Asp Ile
                85                  90                  95

Asp Ala Lys Asp Leu Pro Leu Lys Arg Cys Asn His Glu Pro Gly Thr
            100                 105                 110

Val Cys Pro Ile Cys Leu Glu Asp Ala Lys Glu Leu Ala Lys Asp Thr
        115                 120                 125

Leu Ile Ile Leu Arg Glu Glu Leu Gly Phe Glu Asn Ile His Val Val
130                 135                 140

Tyr Ser Gly Arg Gly Tyr His Ile Arg Ile Leu Asp Glu Trp Ala Leu
145                 150                 155                 160

Gln Leu Asp Ser Lys Ser Arg Glu Arg Ile Leu Ala Phe Ile Ser Ala
                165                 170                 175

Ser Glu Ile Glu Asn Val Glu Glu Phe Arg Arg Phe Leu Leu Glu Lys
            180                 185                 190

Arg Gly Trp Phe Val Leu Lys His Gly Tyr Pro Arg Val Phe Arg Leu
        195                 200                 205

Arg Leu Gly Tyr Phe Ile Leu Arg Val Asn Val Pro His Leu Leu Ser
    210                 215                 220

Ile Gly Ile Arg Arg Asn Ile Ala Lys Lys Ile Leu Asp His Lys Glu
225                 230                 235                 240

Glu Ile Tyr Glu Gly Phe Val Arg Lys Ala Ile Leu Ala Ser Phe Pro
                245                 250                 255

Glu Gly Val Gly Ile Glu Ser Met Ala Lys Leu Phe Ala Leu Ser Thr
            260                 265                 270

Arg Phe Ser Lys Ala Tyr Phe Asp Gly Arg Val Thr Val Asp Ile Lys
        275                 280                 285

Arg Ile Leu Arg Leu Pro Ser Thr Leu His Ser Lys Val Gly Leu Ile
    290                 295                 300

Ala Thr Tyr Val Gly Thr Lys Glu Arg Glu Val Met Lys Phe Asn Pro
305                 310                 315                 320

Phe Arg His Ala Val Pro Lys Phe Arg Lys Glu Val Arg Glu Ala
                325                 330                 335

Tyr Lys Leu Trp Arg Glu Ser Leu Glu Tyr Glu
            340                 345

<210> SEQ ID NO 2
<211> LENGTH: 396
<212> TYPE: PRT
<213> ORGANISM: Pyrococcus furiosus

<400> SEQUENCE: 2

Met Leu Asp Pro Phe Ser Glu Lys Ala Lys Glu Leu Leu Lys Glu Phe
1               5                   10                  15

Gly Ser Met Asn Glu Phe Leu Gln Ala Ile Pro Ser Leu Val Asp Ile
            20                  25                  30

Glu Glu Val Met Asn Arg Leu Lys Phe Ala Lys Glu Ser Glu Ile Ser
```

```
                35                  40                  45
Glu Asp Ile Leu Asn Ile Glu Asp Ile Arg Asp Leu Ala Ser Phe Tyr
 50                  55                  60

Ala Gln Ile Gly Ala Leu Ala Tyr Ser Pro Tyr Gly Leu Glu Leu Glu
 65                  70                  75                  80

Leu Val Lys Lys Ala Asn Leu Arg Ile Tyr Thr Glu Arg Ile Arg Arg
                 85                  90                  95

Arg Arg Lys Ile Arg Ser Asp Glu Ile Gly Ile Glu Val Lys Ile Ala
                100                 105                 110

Val Glu Phe Pro Glu Asn Asp Ile Lys Thr Leu Glu Lys Val Tyr Gly
                115                 120                 125

Gly Leu Pro Glu Tyr Ile Val Ser Leu Arg Glu Phe Leu Asp Leu Val
130                 135                 140

Pro Asp Glu Lys Leu Ser Ser Tyr Val Tyr Asp Gly Asn Val Tyr
145                 150                 155                 160

Leu Arg Lys Asp Asp Leu Leu Lys Val Trp Ser Lys Ala Phe Glu Arg
                165                 170                 175

Asn Val Glu Lys Ala Val Asn Ile Ile Tyr Glu Ile Arg Asp Glu Leu
                180                 185                 190

Pro Glu Phe Tyr Arg Arg Leu Ala Gly Glu Ile Arg Ser Phe Ala Glu
                195                 200                 205

Lys Glu Phe Ser Asp Lys Phe Arg Glu Val Gln Ala Gly Glu Leu Lys
                210                 215                 220

His His Leu Phe Pro Pro Cys Val Lys Asn Ala Leu Arg Gly Val Pro
225                 230                 235                 240

Gln Gly Met Arg Asn Tyr Ala Ile Thr Val Leu Leu Thr Ser Phe Leu
                245                 250                 255

Ser Tyr Ala Arg Ile Cys Pro Asn Pro Pro Arg Arg Asn Val Lys Ile
                260                 265                 270

Arg Asp Cys Ile Lys Asp Met Arg Val Ile Thr Glu Glu Ile Leu Pro
                275                 280                 285

Ile Ile Ile Glu Ala Gly Asn Arg Cys Ser Pro Pro Leu Phe Glu Asp
290                 295                 300

Gln Pro Asn Glu Ile Lys Asn Ile Trp Tyr His Leu Gly Phe Gly Tyr
305                 310                 315                 320

Thr Ala Asn Pro Thr Leu Glu Asp Ser Gly Asn Ser Thr Trp Tyr Phe
                325                 330                 335

Pro Pro Asn Cys Asp Lys Ile Lys Ala Asn Ala Pro Gln Leu Cys Thr
                340                 345                 350

Pro Asp Lys His Cys Arg Tyr Ile Arg Asn Pro Leu Thr Tyr Tyr Leu
                355                 360                 365

Arg Arg Leu Tyr Leu Glu Glu Lys Arg Arg Ala Lys His Ala Asp Glu
370                 375                 380

Gly Ser Asp Lys Gly Gly Lys Glu Arg Ile Leu Gln
385                 390                 395

<210> SEQ ID NO 3
<211> LENGTH: 1044
<212> TYPE: DNA
<213> ORGANISM: Pyrococcus furiosus
<220> FEATURE:
<221> NAME/KEY: exon
<222> LOCATION: (1)..(1041)

<400> SEQUENCE: 3
```

-continued

| | |
|---|---|
| atg ctg atg agg gaa gtg aca aag gag gaa agg agc gaa ttc tac agt<br>Met Leu Met Arg Glu Val Thr Lys Glu Glu Arg Ser Glu Phe Tyr Ser<br>1               5                   10                  15 | 48 |
| aaa gaa tgg agt gca aag aaa ata cca aag ttc ata gtg gac act cta<br>Lys Glu Trp Ser Ala Lys Lys Ile Pro Lys Phe Ile Val Asp Thr Leu<br>            20                  25                  30 | 96 |
| gaa agt aga gaa ttc ggc ttc gat cat aac ggg gaa ggt cca agt gac<br>Glu Ser Arg Glu Phe Gly Phe Asp His Asn Gly Glu Gly Pro Ser Asp<br>        35                  40                  45 | 144 |
| agg aaa aat caa tat tct gac ata aga gat tta gag gac tac att aga<br>Arg Lys Asn Gln Tyr Ser Asp Ile Arg Asp Leu Glu Asp Tyr Ile Arg<br>    50                  55                  60 | 192 |
| gcc aca tcc ccc tac gca gta tat tca agt gtg gca ttt tat gaa aac<br>Ala Thr Ser Pro Tyr Ala Val Tyr Ser Ser Val Ala Phe Tyr Glu Asn<br>65                  70                  75                  80 | 240 |
| ccc agg gag atg gaa ggg tgg aga gga gct gag tta gtt ttt gac att<br>Pro Arg Glu Met Glu Gly Trp Arg Gly Ala Glu Leu Val Phe Asp Ile<br>                85                  90                  95 | 288 |
| gat gcc aag gat ctc ccc cta aag agg tgc aac cac gaa cct ggg aca<br>Asp Ala Lys Asp Leu Pro Leu Lys Arg Cys Asn His Glu Pro Gly Thr<br>            100                 105                 110 | 336 |
| gtg tgt cca ata tgc ctt gaa gat gca aaa gag cta gct aaa gat act<br>Val Cys Pro Ile Cys Leu Glu Asp Ala Lys Glu Leu Ala Lys Asp Thr<br>        115                 120                 125 | 384 |
| cta ata att ctc agg gaa gaa ctc ggc ttt gaa aat atc cat gta gtc<br>Leu Ile Ile Leu Arg Glu Glu Leu Gly Phe Glu Asn Ile His Val Val<br>    130                 135                 140 | 432 |
| tac tcc gga aga gga tat cac ata aga atc cta gat gaa tgg gcc ctc<br>Tyr Ser Gly Arg Gly Tyr His Ile Arg Ile Leu Asp Glu Trp Ala Leu<br>145                 150                 155                 160 | 480 |
| caa ttg gac tcc aaa agt aga gaa aga att ctt gcc ttt att tca gct<br>Gln Leu Asp Ser Lys Ser Arg Glu Arg Ile Leu Ala Phe Ile Ser Ala<br>                165                 170                 175 | 528 |
| agt gaa att gag aac gtt gaa gaa ttt aga aga ttt cta ctg gag aag<br>Ser Glu Ile Glu Asn Val Glu Glu Phe Arg Arg Phe Leu Leu Glu Lys<br>            180                 185                 190 | 576 |
| aga gga tgg ttt gtg tta aag cat ggc tac ccg aga gta ttt agg ttg<br>Arg Gly Trp Phe Val Leu Lys His Gly Tyr Pro Arg Val Phe Arg Leu<br>        195                 200                 205 | 624 |
| aga ctg gga tac ttt att cta agg gtt aac gta cct cac ttg cta agc<br>Arg Leu Gly Tyr Phe Ile Leu Arg Val Asn Val Pro His Leu Leu Ser<br>    210                 215                 220 | 672 |
| att gga ata aga aga aat att gca aag aaa att cta gat cac aaa gaa<br>Ile Gly Ile Arg Arg Asn Ile Ala Lys Lys Ile Leu Asp His Lys Glu<br>225                 230                 235                 240 | 720 |
| gaa ata tac gag gga ttt gta agg aag gca ata ttg gca tct ttt cca<br>Glu Ile Tyr Glu Gly Phe Val Arg Lys Ala Ile Leu Ala Ser Phe Pro<br>                245                 250                 255 | 768 |
| gaa ggc gtg gga att gaa agc atg gct aag ctc ttt gcc cta tca act<br>Glu Gly Val Gly Ile Glu Ser Met Ala Lys Leu Phe Ala Leu Ser Thr<br>            260                 265                 270 | 816 |
| aga ttt tca aag gcc tat ttt gat ggt agg gtt aca gtt gat ata aag<br>Arg Phe Ser Lys Ala Tyr Phe Asp Gly Arg Val Thr Val Asp Ile Lys<br>        275                 280                 285 | 864 |
| aga atc cta agg ttg ccc tca aca ctc cat tcc aaa gtg ggc ctt ata<br>Arg Ile Leu Arg Leu Pro Ser Thr Leu His Ser Lys Val Gly Leu Ile<br>    290                 295                 300 | 912 |
| gca act tat gtt gga acc aag gag aga gag gtc atg aag ttt aat cca<br>Ala Thr Tyr Val Gly Thr Lys Glu Arg Glu Val Met Lys Phe Asn Pro<br>305                 310                 315                 320 | 960 |

```
ttt aga cat gca gtg cca aag ttc agg aaa aaa gaa gtg cgc gaa gct    1008
Phe Arg His Ala Val Pro Lys Phe Arg Lys Lys Glu Val Arg Glu Ala
                    325                 330                 335 tat aaa ctg tgg aga gag tcc ttg gaa tat gaa taa                    1044
Tyr Lys Leu Trp Arg Glu Ser Leu Glu Tyr Glu
            340                 345

<210> SEQ ID NO 4
<211> LENGTH: 1191
<212> TYPE: DNA
<213> ORGANISM: Pyrococcus furiosus
<220> FEATURE:
<221> NAME/KEY: exon
<222> LOCATION: (1)..(1188)

<400> SEQUENCE: 4 atg cta gac cca ttt agt gag aag gcc aaa gaa cta cta aaa gaa ttc    48
Met Leu Asp Pro Phe Ser Glu Lys Ala Lys Glu Leu Leu Lys Glu Phe
1               5                   10                  15 gga tca atg aat gaa ttc ctt caa gct atc ccc tct ctt gtg gat ata    96
Gly Ser Met Asn Glu Phe Leu Gln Ala Ile Pro Ser Leu Val Asp Ile
                20                  25                  30 gag gaa gtc atg aat agg tta aaa ttt gca aaa gaa tcc gaa atc tcc   144
Glu Glu Val Met Asn Arg Leu Lys Phe Ala Lys Glu Ser Glu Ile Ser
            35                  40                  45 gaa gat att ctg aat ata gag gat ata cga gat tta gca agc ttt tat   192
Glu Asp Ile Leu Asn Ile Glu Asp Ile Arg Asp Leu Ala Ser Phe Tyr
        50                  55                  60 gcc caa ata gga gca tta gct tac tcc cca tat gga ctg gaa ttg gaa   240
Ala Gln Ile Gly Ala Leu Ala Tyr Ser Pro Tyr Gly Leu Glu Leu Glu
65                  70                  75                  80 cta gta aag aag gct aat ttg aga ata tat aca gag aga atc cgc aga   288
Leu Val Lys Lys Ala Asn Leu Arg Ile Tyr Thr Glu Arg Ile Arg Arg
                85                  90                  95 aga agg aaa ata agg agc gat gaa att gga att gaa gta aaa ata gca   336
Arg Arg Lys Ile Arg Ser Asp Glu Ile Gly Ile Glu Val Lys Ile Ala
            100                 105                 110 gtt gaa ttc cca gaa aac gac ata aaa aca ctt gaa aaa gtc tat ggt   384
Val Glu Phe Pro Glu Asn Asp Ile Lys Thr Leu Glu Lys Val Tyr Gly
        115                 120                 125 ggc ctt cca gaa tac ata gtt tcc cta agg gag ttt tta gat cta gtt   432
Gly Leu Pro Glu Tyr Ile Val Ser Leu Arg Glu Phe Leu Asp Leu Val
    130                 135                 140 cca gat gaa aaa ctc tcc tct tat tac gtc tat gat ggg aat gtg tat   480
Pro Asp Glu Lys Leu Ser Ser Tyr Tyr Val Tyr Asp Gly Asn Val Tyr
145                 150                 155                 160 tta agg aag gat gac ctc tta aaa gtg tgg agc aaa gct ttt gag aga   528
Leu Arg Lys Asp Asp Leu Leu Lys Val Trp Ser Lys Ala Phe Glu Arg
                165                 170                 175 aac gtt gaa aag gcc gtg aat ata att tac gaa ata agg gac gag ctt   576
Asn Val Glu Lys Ala Val Asn Ile Ile Tyr Glu Ile Arg Asp Glu Leu
            180                 185                 190 cca gag ttt tat aga aga ctt gca gga gag ata aga tct ttt gcc gag   624
Pro Glu Phe Tyr Arg Arg Leu Ala Gly Glu Ile Arg Ser Phe Ala Glu
        195                 200                 205 aaa gaa ttt tca gat aag ttt aga gag gtt caa gca gga gaa cta aaa   672
Lys Glu Phe Ser Asp Lys Phe Arg Glu Val Gln Ala Gly Glu Leu Lys
    210                 215                 220 cac cat cta ttc cct ccc tgt gtt aaa aat gct ctc aga gga gtt cca   720
His His Leu Phe Pro Pro Cys Val Lys Asn Ala Leu Arg Gly Val Pro
225                 230                 235                 240
```

```
cag gga atg agg aac tat gca ata acg gta ttg ctc acg agc ttt cta      768
Gln Gly Met Arg Asn Tyr Ala Ile Thr Val Leu Leu Thr Ser Phe Leu
                245                 250                 255 agc tat gca agg ata tgt cca aat cct ccc agg aga aat gta aaa att      816
Ser Tyr Ala Arg Ile Cys Pro Asn Pro Pro Arg Arg Asn Val Lys Ile
            260                 265                 270 agg gac tgc att aaa gat atg agg gta ata acc gag gaa ata ctt ccc      864
Arg Asp Cys Ile Lys Asp Met Arg Val Ile Thr Glu Glu Ile Leu Pro
        275                 280                 285 ata ata ata gag gcc ggg aac aga tgc tca cct cca cta ttc gaa gat      912
Ile Ile Ile Glu Ala Gly Asn Arg Cys Ser Pro Pro Leu Phe Glu Asp
    290                 295                 300 caa cca aac gaa ata aag aat ata tgg tac cac ttg ggc ttt gga tac      960
Gln Pro Asn Glu Ile Lys Asn Ile Trp Tyr His Leu Gly Phe Gly Tyr
305                 310                 315                 320 act gca aat cct acc ctt gaa gac agc ggg aac tca aca tgg tac ttt     1008
Thr Ala Asn Pro Thr Leu Glu Asp Ser Gly Asn Ser Thr Trp Tyr Phe
                325                 330                 335 ccc cct aac tgt gat aag ata aag gca aat gct cca cag ctt tgc act     1056
Pro Pro Asn Cys Asp Lys Ile Lys Ala Asn Ala Pro Gln Leu Cys Thr
            340                 345                 350 cct gac aag cac tgc aga tac att aga aat ccc cta aca tat tat cta     1104
Pro Asp Lys His Cys Arg Tyr Ile Arg Asn Pro Leu Thr Tyr Tyr Leu
        355                 360                 365 agg cgt ctt tac tta gaa gag aag agg agg gcc aag cat gct gat gag     1152
Arg Arg Leu Tyr Leu Glu Glu Lys Arg Arg Ala Lys His Ala Asp Glu
    370                 375                 380 gga agt gac aaa gga gga aag gag cga att cta cag taa                 1191
Gly Ser Asp Lys Gly Gly Lys Glu Arg Ile Leu Gln
385                 390                 395

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
catatgctga tgagggaagt gacaaaggag                                      30

<210> SEQ ID NO 6
<211> LENGTH: 31
<212> TYPE: DNA
<213> ORGANISM: Artificial Sequence
<220> FEATURE:
<223> OTHER INFORMATION: PCR primer

<400> SEQUENCE: 6
ctcgagcctt tattcatatt ccaaggactc t                                    31

<210> SEQ ID NO 7
<211> LENGTH: 28
<212> TYPE: DNA
<213> ORGANISM: Artificial Sequence
<220> FEATURE:
<223> OTHER INFORMATION: PCR primer

<400> SEQUENCE: 7
cacgaccatg gtagacccat ttagtgag                                        28

<210> SEQ ID NO 8
```

```
-continued

<211> LENGTH: 30
<212> TYPE: DNA
<213> ORGANISM: Artificial Sequence
<220> FEATURE:
<223> OTHER INFORMATION: PCR primer

<400> SEQUENCE: 8
cacggtcgac tcattactgt agaattcgct                              30

<210> SEQ ID NO 9
<211> LENGTH: 49
<212> TYPE: DNA
<213> ORGANISM: Artificial Sequence
<220> FEATURE:
<223> OTHER INFORMATION: Probe

<400> SEQUENCE: 9
agctaccatg cctgcacgaa ttaagcaatt cgtaatcatg gtcatagct          49
```

US 7,211,647 B2

DNA SYNTHETASE

This application is a 371 of PCT/JP01/06465, filed Jul. 27, 2001; the disclosure of which is incorporated herein by reference.

TECHNICAL FIELD

The present invention relates to a new protein that is useful as a genetic engineering reagent and a method to produce the protein.

BACKGROUND ART

A DNA polymerase that synthesizes DNA chain having a sequence that is complementary to base sequence of the template DNA is used commonly as an essential reagent for genetic engineering experiments like PCR (Polymerase Chain Reaction), a base determination of DNA, a site-specific mutagenesis, and so on. Contribution of the enzyme to the progress of molecular medicine, molecular biology, and biochemistry is enormous.

To examine the enzyme called a DNA polymerase closely, biochemical character of each enzyme is different, and various DNA polymerases are sold in the market until now. Each enzyme has different characteristics like thermo stability, synthesized chain elongation ability, ability to proofread wrong base in synthesizing, preference of a template DNA, and they are selected according to the object of the experiment.

However, these enzymes are not sufficient to satisfy all the objects of experiments. More suitable new DNA polymerase is desired to be developed to each object. Also, as the basic characteristic of DNA polymerase, short chains of nucleotides, a primer, are essential in order to start DNA synthesis reaction, so the PCR needs a pair of site-specific primers for amplification area, and, it is necessary to prepare the primer that amplifies target area and the primer needs to be added to a reaction mixture for each experiment.

DISCLOSURE OF THE INVENTION

The object of the present invention is to identify gene for new DNA synthetase and to provide the new DNA synthetase having a new biochemical characteristic, as a reagent for genetic engineering.

The present invention relates to proteins that show DNA primase activity and DNA polymerase activity.

The "DNA primase activity" described in the present specification means an ability to synthesize a DNA chain with substrate described below by depending on a template DNA chain when a DNA chain that could be a template and deoxynucleotide triphosphate that could be substrate is present. In the same way, the "DNA polymerase activity" means an ability to synthesize a DNA chain from 3' terminal of a primer with substrate described below by depending on a template DNA chain when a template-primer, template DNA chain that is bound with its complementary oligodeoxynucleotide (primer), and deoxynucleotide triphosphate that could be substrate is present. This is the first time that a protein having both DNA primase activity and DNA polymerase activity was found.

This protein could be derived from eukaryotes including mammals, or prokaryotes including archaebacteria, eubacteria. In the preferred embodiment, this protein derives from archaebacteria, and having thermo stability. In the present invention, protein that has "thermo stability" means, the protein could preserve the activities under temperature of 50° C. or more.

In a one embodiment, the protein includes amino acid sequence shown in SEQ ID NO: 1. In another embodiment, the protein may includes amino acid sequence wherein one or several amino acids are deleted, replaced or added in amino acid sequence shown in SEQ ID NO: 1.

In the present specification, these proteins are sometimes called "protein 1".

The present invention also relates to a protein that could enforces the DNA primase activity and/or the DNA polymerase activity by forming a complex with the protein that is described above. This protein could be derived from eukaryotes including mammals, or prokaryotes including archaebacteria, eubacteria. In case of the preferred embodiment, this protein derives from an archaebacteria, and having thermo stability. In one embodiment, the protein includes amino acid sequence shown in SEQ ID NO: 2. The protein may includes amino acid sequence wherein one or several amino acids are deleted, replaced or added in amino acid sequence shown in SEQ ID NO: 2.

In the present specification, these proteins are sometimes called "protein 2".

BEST MODE OF CARRYING OUT THE INVENTION

Figure 1:
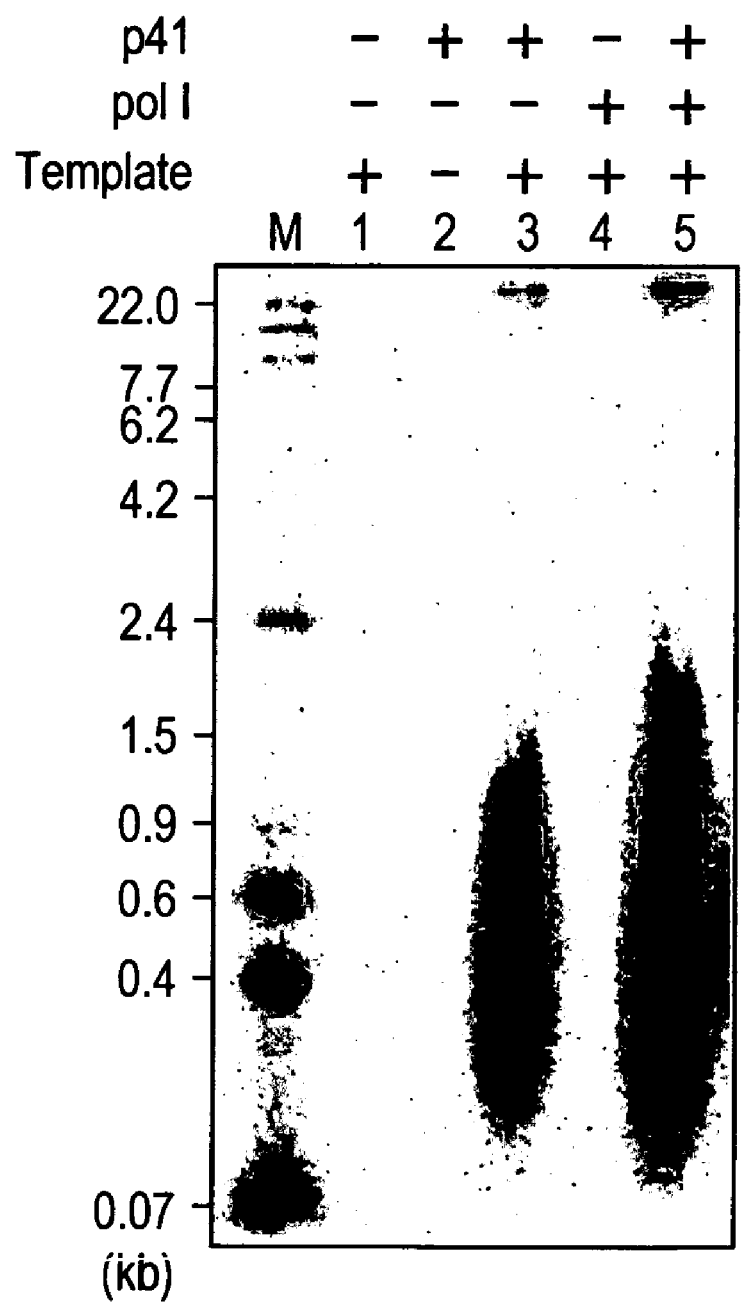
FIG. 1 is a photograph showing DNA primase activity of p41. This is an autoradiography of the product separated by electrophoreting with alkaline agarose gel after a reaction according to a method described in Example 5. When the template DNA existed, p41 synthesized 0.4 to 0.6 kilo base pairs of DNA chain. When DNA polymerase I was added together, longer chain product was detected.

The inventors of the present invention set their goal to isolate DNA synthetase that has excellent characteristic as a genetic engineering reagent, especially thermo stability, and screened hyperthermophilic archaebacteria. In the genome sequence of *Pyrococcus furiosus,* which was isolated and identified as hyperthermophilic archaebacteria, there are genes that may code similar sequence to eukaryote DNA primase. Also, investigating this gene area, another gene was found just next to this area, and it was predicted that these gene areas form operon. Accordingly, the inventers of the present invention cloned these genes (SEQ ID NO: 3 and 4), and produced and purified the coded proteins, and identified biochemical characteristic of these proteins. The purified proteins are named p41 (SEQ ID NO: 1) and p46 (SEQ ID NO: 2).

DNA primer synthesizing (primase) activity was detected from p41 in vitro reaction. Further, contrary to what had expected, p41 showed strong primer extending activity that is as strong as a conventional DNA polymerase. These activities are very stable under heat and have a great potential to be utilized as an amplification enzyme for gene. It is especially notable that the protein has the activity to synthesize DNA chain without primer. In order to amplify the target gene area, the current PCR technique needs to make a specific primer for each area, and add them to the reaction mixture. The enzyme of the present invention has a DNA-synthesizing activity and does not need a primer, so the new gene amplification technique could be provided. The inventors also found out that a protein derived from hyperthermophilic archaebacteria *Aeropyrum pernix* has same characteristic and shows the DNA primase activity and the DNA polymerase activity.

No DNA synthesis reaction was detected by p46 alone, but it was found that p46 formed stable complex with p41, and contributes to increase affinity to DNA. DNA synthesizing activity that is independent from primer in p41–p46 complex showed much higher rate compared to p41 alone. Also, p41–p46 complex can synthesize RNA primer even though it is not so effective.

Therefore, the present invention is a method to polymerize deoxynucleotide triphosphate and also relates to, 1) provide DNA chain as template DNA and deoxynucleotide triphosphate as substrate,
2) add protein 1 and polymerize deoxynucleotide triphosphate.

The protein 2 can be added in this polymerization method besides the protein 1. The protein 2 enforces the DNA primase activity of the protein 1.

The present invention is also a method to polymerize deoxynucleotide triphosphate and also relates to, 1) provide DNA chain as template DNA and deoxynucleotide triphosphate as substrate,
2) add complementary oligodeoxynuclotide (primer) to DNA chain as template DNA and form complex with the DNA chain,
3) add protein 1 and polymerize deoxynucleotide triphosphate.

The protein 2 can be added in this polymerization method besides the protein 1. The protein 2 enforces the DNA polymerase activity of the protein 1.

As mentioned above, the inventors has identified the unkown two proteins,the former that has both the DNA primase activity and the DNA polymerase activity, and the latter that enforces the DNA polymerase activity of the former one. These proteins are used for a new genetic engineering method which utilizes the DNA synthesis reaction.

The protein 1 or 2 according to the present invention are synthesized recombinant DNA method described below:

1) prepare a base sequence that codes the protein 1 or 2,
2) insert the base sequence to an expression vector,
3) transform host cell by the vector,
4) cultivate the transformant, and
5) isolate desired protein from the culture.

SEQ ID NO: 3 is shown as an example for the base sequence that codes the protein 1. It is well known that many other base sequences can be used to code protein 1 by degeneration of genetic codes.

SEQ ID NO: 4 is shown as an example for the base sequence that codes the protein 2. It is well known that many other base sequences can be used to code protein 2 by degeneration of genetic codes.

To make purification of the expressed protein easier, or for other purposes, it is possible to express the protein of the present invention as the fusion protein of the protein in the present invention and other proteins or peptides. In that case, base sequence that codes the proteins of the present invention needs binding method with base sequences that code other proteins or peptides by appropriate.

The present invention relates to a vector, especially a plasmid, a cosmid, a virus, a bacteriophage, and other vectors that are generally used for genetic engineering. By using methods that are well known to those skilled in the art, the varieties of plasmids and vectors are build. (For example, refer to the technique described in Sambrook, Molecular Cloning A Laboratory Manual, Cold spring Harbor Laboratory (1989) and Ausbel, Current Protocols in Molecular Biology, Green Publishing Associates and Wiley Interscience, N.Y. (1994)). According to the present invention, the plasmids and vectors that are preferably used include the plasmids and vectors that are well known to those skilled in the art.

In the preferred embodiments, a DNA sequence that codes a protein of the present invention inside vector binds in active state with the control sequence that is needed in order to express genes in procaryotic or eukaryotic cell.

The word "control sequence" means a control DNA sequence that is needed to express the code sequence that binds with. Characteristic of such a control sequence changes by a host. The control sequence in prokaryote cell generally includes a promoter, a ribosome binding site and terminator. The control sequence in eukaryotic cell includes a promoter, a terminator, and in some cases, a transactivator, or a transcription factors. The word "control sequence" intends to include all the elements that are needed to express its presence by the smallest unit. Also it is possible for the "control sequence" to include some other useful elements.

The word "binds in active state" means each of the elements is in a position that is possible to work in the intended method. The control sequence that "binds in active state" to the control sequence is bound by a method that can achieve the expression of codes, and the condition is in the same range as the control sequence. In case the control sequence is a promoter, fact that the double-stranded DNA is favored is well known to those skilled in the art.

Therefore, a vector that is used for the present invention is an expression vector. The "expression vector" is a construction that transforms a selected host cell, and expresses the code sequence inside the selected host cell. The expression vector may be, for example, a cloning vector, a binary vector, or an integrating vector. The expression favorably includes a transcription of the nucleic acid molecule to mRNA which is possible to translate.

A controlling element that ensures the expression inside the prokaryote cells and/or eukaryote cells is well known to those skilled in the art. In the case of eukaryote cells, the controlling element usually includes a promoter that ensures starting of the normal transcription and poly (A) signal that ensures the end of transcription and stability of transcript. The promoters that are used in general are a polyubiquitin promoter and an actin promoter. Further, the controlling element may include transcription or translation enhancer.

Examples of the possiblecontrolling element that enables the expression in prokaryote cells are PL, lac, trp or tac promoters for E. Coli. In the eukaryote cells, examples of the possible controlling elements that enable the expression includes AOX1 or GAL1 promoters for yeast, and CMV-, SV40-, RSV-promoters (Rous Sarcoma virus) are CMV enhancer, SV40 enhancer or globin intron for mammals and other animal cells. The expression vectors that are appropriate and well known to those skilled in the art are the expression vector pcDV1 (Pharmacia) by Okayama-Berg, pCDM8, pRc/CMV, pcDNA1, pcDNA3 (In-vitrogen), pSPORT1 (GIBCO BRL), and so on.

In the preferred embodiment, the vector in the present invention that is described above includes selectable markers.

Further, the present invention relates to a host cell that includes a vector described above. Sequence of nucleic acid is foreign to the host cell.

The word "foreign" means the nucleic acid molecule is heterologous (it means that the nucleic acid molecule derives from different cell or a creature having different genetic background) to the host cell, or the nucleic acid molecule is homologus to the host cell, but in a different genetic environment from the counterpart that is naturally present in the nucleic acid molecule. That means, if the nucleic acid molecule is homologus relating to the host cell, the nucleic acid molecule in host cell is not in natural gene position. In this case, the nucleic acid molecule is in control under the promoter of itself, or can be under the control of heterologous promoter. The vector or the promoter of the present invention inside host cell can be introduced into genome of the host cell or kept outside chromosomes.

Therefore, the present invention relates to the host cell that includes a vector or genes of the present invention. The host cell can be prokaryote or eucaryote cell, for example eubacteria, archaebacteria, insects, fungi, plants, or animal cells etc. Favorable fungi cells are, for example, cell of genus *Saccharomycess*, especially *Saccharomycess cerevisiae*.

The word "prokaryote" intends all the bacteria that can be transformed or transfected by DNA or RNA to express the protein of the present invention. Examples of prokaryotic host cells are gram positive and negative bacteria like *E. coli, S. typhimurium, Serratia marcescens,* or *Bacillus subtilis,* and may include archaebacteria *Methanococcus maripaludis,* or *Haloferax volvanii*.

The word "eukaryote" intends to include yeast, higher plants, insects, and favorably, cells of mammals. For the host cells used for recombination producing method, the protein that is coded by the polynucleotides of the present invention may be glycosylated or may be not. The protein of the present invention may or may not have the first amino acid residue.

Using one of the techniques well known to those skilled in the art, genes of the present invention is transformed, or transfected. Further, production method for fused, or functionally bound gene and also a method to express the gene inside for example, mammals or bacteria is well known to those skilled in the art (Sambrook, Molecular Cloning: A Laboratory Manual, Cold Spring Harbor Laboratory, Cold Spring Harbor, N.Y., 1989).

The recombinant *Escherichia coli* bacteria that is used to produce new protein described in the present invention is named and expressed as *Escherichia coli* BL21(DE3)RIL/pPFPR41 and *Escherichia coli* BL21(DE3)RIL/pPFPR46. These *Escherichia coli* bacteria are deposited to the National Institute of Advanced Industrial Science and Technology as accession number FERM BP-7650 and FERM BP-7651, respectively.

Embodiments of the present invention will be explained in detail below. It should be noted that the present invention is not limited to the below-explained embodiments.

EXAMPLES

Example 1

Preparing Genomic DNA of *Pyrococcus furiosus*

*P. furiosus* DSM3638 was obtained from Deutsche Sammlung von Mikroorganismen und Zelkulturen GmbH and cultured by the method described in the document (Nucleic Acids Research, Vol. 21 p259–265). 1.2 g of cell body was extracted from 500 ml of culture solution. The extracted cell body was suspended with 10 ml buffer L (10 mM Tris-HCl (pH8.0), 1 mM EDTA, 100 mM NaCl), and added 1 ml of 10% SDS. After the suspension was stirred, 50 µl of proteinase K (20 mg/ml) was added, and the suspension was left still for 60 minutes under temperature of 55° C. Then the reaction mixture went under the process of phenol extraction, phenol extraction/chloroform extraction, and chloroform extraction sequentially. DNA was then insolubilized by adding ethanol. Collected DNA was dissolved in 1 ml of TE (10 mM Tris-HCl, pH8.0, 1 mM EDTA), and reacted with 0.75 mg of RNase A for 60 minutes under temperature of 37° C. Then the reaction mixture goes under the process of phenol extraction, phenol extraction/chloroform extraction, and chloroform extraction sequentially. DNA was collected by the ethanol precipitation. DNA was then insolubilized by adding ethanol. 0.75 mg of DNA is collected.

Example 2

To clone the target gene from the genome DNA of the *Pyrococcus furiosus*, an adequate primer was synthesized. As the gene amplifier of p41, (SEQ ID NO:5)
5'CATATGCTGATGAGGGAAGTGACAAAGGAG-3'

(SEQ ID NO:6)
5'CTCGAGCCTTTATTCATATTCCAAGGACTCT-3' were used as the forward and reverse primer. For amplifying the gene p46, (SEQ ID NO:7)
5'-CACGACCATGGTAGACCCATTTAGTGAG-3'

(SEQ ID NO:8)
5'-CACGGTCGACTCATTACTGTAGAATTCGCT-3' were used as the primers. PCR was used under normal composition, the time and temperature of one cycle was 30 seconds with 95° C., 30 seconds with 55° C., 30 seconds with 72° C. for 30 cycles. The amplified DNA chain was inserted to pT7 blue vector (Novagen, Inc) and recombinant plasmid was isolated. The primers were provided with a recognition sequence that recognizes restriction enzymes NdeI, XhoI (p41), or NdeI, SalI (p46) respectively. By digesting DNA with those enzymes, only the target part was cut. The target part was integrated to expression vector pET type with ATG in the NdeI sequence of the target part as an initiation codon for translation. The p41 and p46 genes (SEQ ID NO: 3 and 4) were inserted to pET28a' (pET28a originally has kanamycin resistance gene as a selectable marker but it is replaced with ampicillin resistant marker for convenience) and pET21a. The plasmids were named pPFPR41 and pPFPR46. By constructing such plasmids, p41 was produced in a form with a tag having six histidine connected to N-terminal, and p46 was produced in a form that start with the original initiation codon ATG when they were translated.

Example 3

Production and Purification of p41 Protein

The plasmid pPFPR41 was inserted to *Escherichia coli* BL21(DE3)RIL, cultured the transformant that was obtained, and produced the target protein.

The *Escherichia coli* BL21(DE3)RIL/pPFPR41 was cultured in 500 ml of LB culture (tryptone 10 g/l, yeast extract 5 g/l, NaCl 5 g/l, pH7.2) with 100 μg/ml concentration of ampicillin and 20 μg/ml concentration of chloramphenicol. When turbidity of the culture became $0.4A_{600}$, inducer, isopropyl-β-D-thiogalactoside (IPTG), was added and then cultured for five hours. After collecting cell bodies, the cell bodies were suspended with 40 ml buffer A (50 mM Tris-HCl, pH 8.0, 0.1 mM EDTA, 2 mM β-mercaptoethanol) and 1 ml of phenylmethylsulfonyl fluoride (PMSF). The suspension was put to ultrasonic disintegrator. Supernatant of the extraction was collected after 20 minutes of centrifugal separation by 16,000 rpm, and boiled for 15 minutes with 80° C. Almost all of the protein derived from Escherichia coli was denatured and insolubilized. Then the supernatant was collected by using the centrifugal separation and poured onto the metal resin ($Co^{2+}$) chelating column (TALON, Clontech Laboratories Inc.). The proteins that were not conjugated were washed and removed by the buffer A including 10 mM of imidazole. Then the connected proteins with histidine tag on it were eluted by make the concentration rate of the imidazole higher to 100 mM. This fraction was poured onto a cation-exchange column (HiTrap SP, Amersham Pharmacia Biotech) and chromatography was carried out with automatic liquid chromatography system (AKTA explorer, pharmacia). It was developed from 0.1 to 0.8 M of NaCl according to linear NaCl gradient slope. The target activity was found at 0.5 to 0.7 M NaCl. The fraction that shows activity was collected and dialyzed with 2 l of the buffer A. Then the dialyzed fraction was purified and sampled. About 1 mg of enzyme was extracted from 1 liter of culture.

Example 4

Production and Purification of p46 Protein

The plasmid pPFPR46 was inserted to *Escherichia coli* BL21(DE3)RIL, cultured the transformant that was obtained, and produced the target protein.

The *Escherichia coli* BL21(DE3)RIL/pPFPR46 was cultured in the same culture as described in the Example 3. After collecting cell bodies, these cell bodies were disintegrated and unrefined extract was collected by centrifugal separation in the method described in the Example 3. Then the extraction was boiled for 15 minutes with 80° C., and only the thermophylactic proteins were collected as the supernatant of the centrifugation. Polyethylenimine (Polymin P) and NaCl were added to this solution for each concentration 0.2% (weight/capacity) and 0.3M. The solution was stirred with ice for 30 minutes. Insolubilized nucleic acid was removed by the centrifugal separation, and aluminum sulfate was added to saturate for 80%. As the result, the proteins were precipitated.

Precipitate were then dissolved to buffer C (50 mM Tris-Cl, pH8.0, 0.3 M NaCl, 1 mM β-mercaptoethanol) and poured onto the anion-exchange column (HiTrapQ, Amersham Pharmacia Biotech) after equilibrating with same buffer C. It was developed from 0.1 to 1 M of NaCl according to linear NaCl gradient slope. The target activity was found at 0.15 to 0.25 M NaCl. The fraction that shows activity was collected for 10 ml and poured into heparin affinity column (HiTrap Heparin, Pharmacia Biotech). It was developed from 0.05 to 0.8 M of NaCl according to linear NaCl gradient slope. The target protein was found at 0.3 to 0.5 M NaCl. About 6.6 mg of enzyme was extracted from 1 liter of culture.

Example 5

Detection of DNA Primase Activity

To detect the primase activity, the occurrence of the DNA synthesizing was detected by tracing radio activity, by using M13 Phage DNA (single-stranded DNA) as a template and adding $^{32}P$-labelled dATP as a part of substrate. Following were added to 50 mM Tris-HCl, pH8.1, 10 mM $MgCl_2$, 1 mM β-mercaptoethanol solution with a concentration of: 0.05 μg/μl of M13DNA, 100 μM of each dCTP, dGTP, dTTP, 10 μM of [α32p] dATP, and 0.7 μM of p41 protein or DNA polymerase I for 2.5 units. 20 μg of this reaction mixture was warmed for 20 minutes in 70° C., and separated by whether electrophoreting with 10% polyacrylamide gel including 8M of urea or electrophoreting with 1% alkaline agarose gel. FIG. 1 shows result of electrophoreting with alkaline agarose gel. P41 protein synthesized 0.4 to 0.6 kbp of DNA chain when DNA template was present (lane 3). DNA polymerase I did not synthesize under this condition because there were no primers present (lane 4). When pol I was added to p41, synthesizing chain became longer (lane 5).

Example 6

Detection of DNA Polymerase Activity

Figure 2:
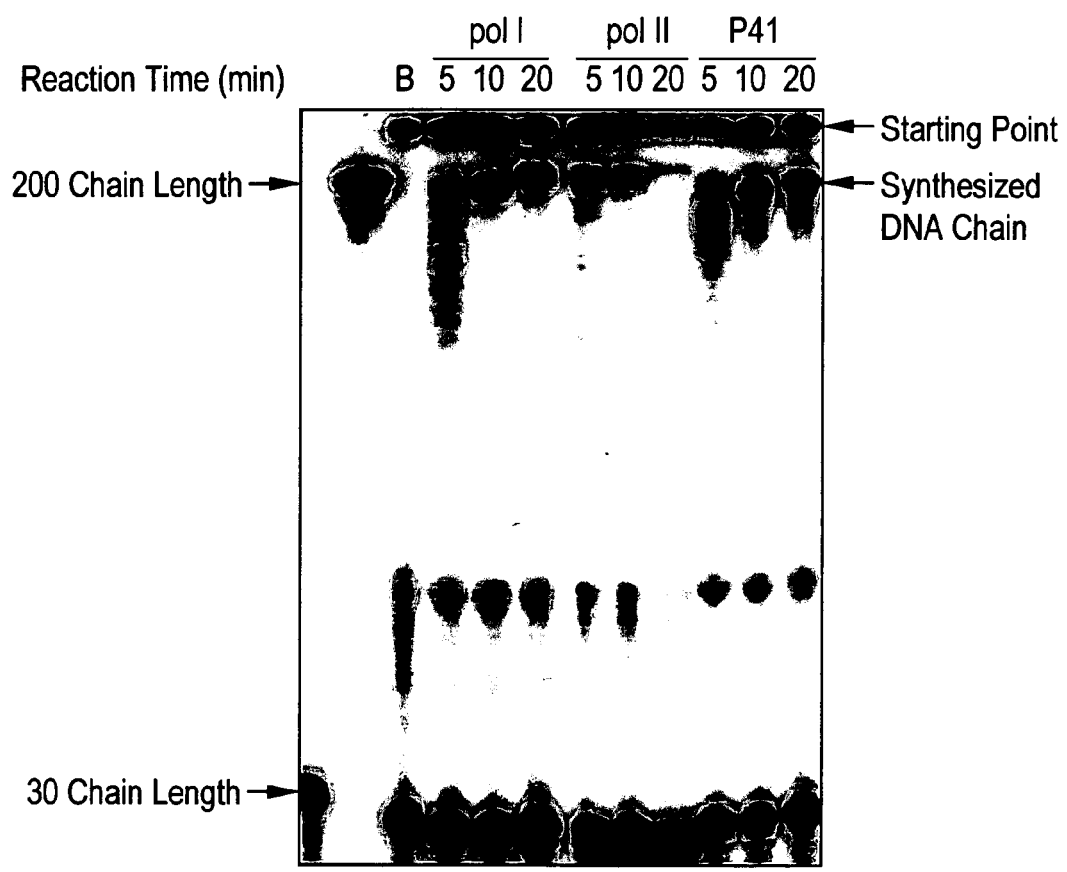
FIG. 2 shows a photograph of primase activity of p41. An autoradiography of the product separated by electrophoreting with 10% polyacrylamide gel including 8M of urea after the reaction according to a method described in Example 5. 30-chain-length primers labelled with radiation were elongated by the p41 as well as DNA polymerases I and II. The synthesized chains were becoming longer as the time elapses.
Figure 3:
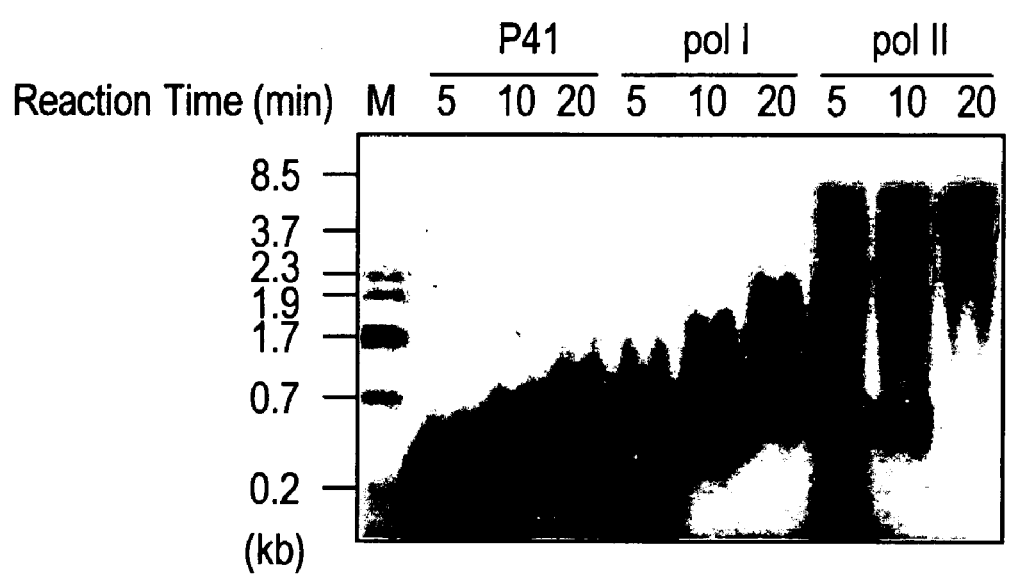
FIG. 3 shows a photograph of primase activity of p41. To analyze reacted products in FIG. 2 more thoroughly, the same reaction mixture was analyzed by electrophoreting with 1% alkaline agarose gel.

To detect the polymerase activity, M13 Phage DNA (single-stranded DNA) was used as a template, and annealed with a primer that was 30 chains long and labelled with $^{32}$P at the 5' terminal. It was then reacted with enzyme sample with dNTP as a substrate. Following were added to 50 mM Tris-HCl, pH8.1, 10 mM MgCl$_2$, 1 mM β-mercaptoethanol solution (20 μl), 0.5 μg of M13DNA that was annealed with the labeled primer, 125 μM of each dCTP, dGTP, dTTP, 0.14 μM of p41 protein. The reaction mixture was warmed for 5, 10, 20 minutes in 70° C., and taken out for 5 μl each, and added with 3 μl of stop solution (95% formamide, 0.05% Bromophenol Blue, 0.05% Xylenecyanol). As the comparison, reaction mixture that was replaced p41 with 2.5 units of DNA polymerase I, or DNA polymerase II was experimented. The reaction mixture were separated by electrophoreting with 10% polyacrylamide gel including 8M of urea or electrophoreting with 1% alkaline agarose gel. Then autoradiography was taken. As the result of electrophoreting with polyacrylamide gel, p41 protein extended 30 chains long primer (FIG. 2), which was as same as publicly known DNA polymerases I and II, so the reaction mixture was electrophoreted with the alkaline agarose gel that enabled an analysis of long chain area (FIG. 3). At least under this condition, primer extending activity that was as equal as publicly known DNA polymerases were found.

Example 7

Forming p41–p46 Complex

Figure 4:
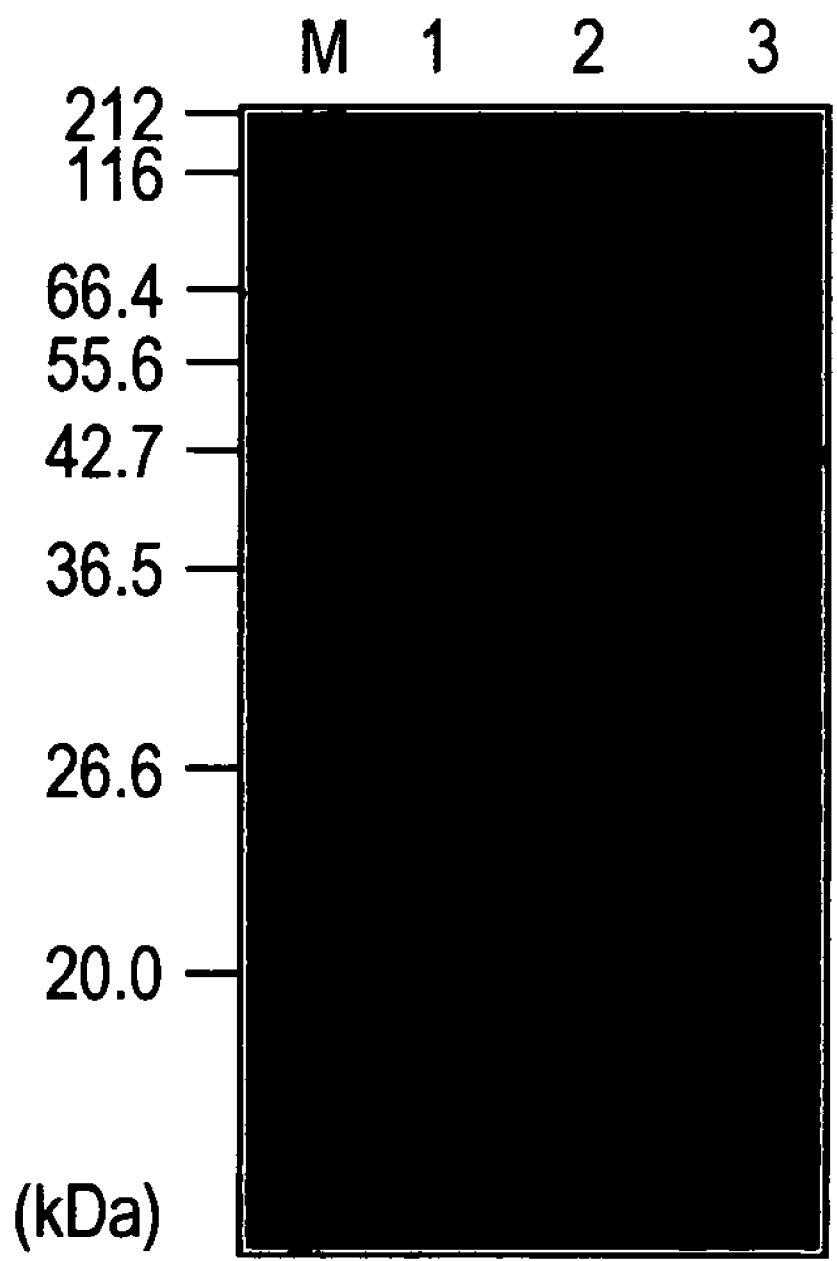
FIG. 4 shows a photograph of p41–p46 complex. A purified p46 was eluted to non-absorption area of a cation exchange column chromatography (lane 3). p41 was absorbed and eluted with about 0.6 M of NaCl (lane 1). Mixing both proteins and set the mixture to the column, both of them were eluted by the same concentration of NaCl (lane 2), which supports that the both proteins would form stable complex.

To make sure the produced p41 and p46 interact, cation-exchange column (HiTrap SP) was used to analyze with a single case, and mixed case. As it was described in the Example 3, P41 protein was trapped by the HiTrap SP column, but p46 passed through under the same condition. When the proteins were mixed and poured onto the column, p46 and p41 were eluted together on a same absorbed fraction (FIG. 4). From this result, it was thought that both proteins formed very stable complex.

Example 8

Increase of DNA Binding Affinity by p46

Figure 5A:
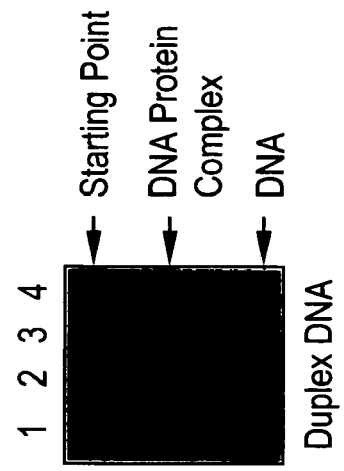
FIG. 5 shows a measurement of affinity to DNA. The purified p41–p46 complex was used to three types of DNA to see avidities. Ratio of protein to DNA was 0, 1, 3, 5, starting from lane 1 to 4. All three types of DNA showed band shift according to the amount of protein.
Figure 5B:
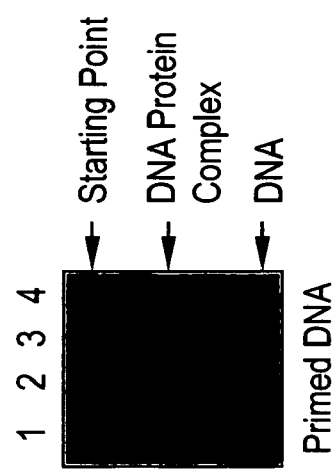
Figure 5C:
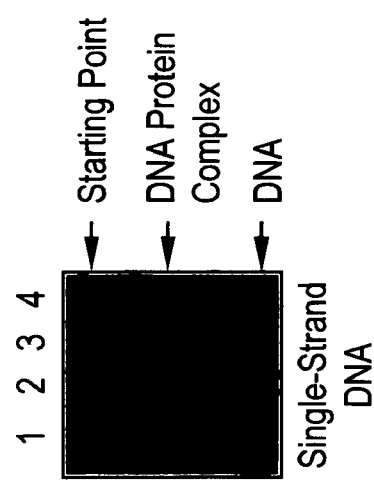

The gel-shift assay was used to detect binding activity that binds enzyme to DNA. 49 chain-length oligodeoxynuclotide, 5'-dAGCTACCATGCCTGCACGAATTAAG-CAATTCGTAATCATGGTCATAGCT-3' (SEQ ID NO:9); was labeled with $^{32}$P at 5' terminal. Then the chain was used for gel-shift assay with itself or annealed with 49 or 17 chain length complementary oligodeoxynuclotide. With these three kinds of DNA, and the proteins were mixed in variety of concentrations in gel-shift assay buffer (50 mM Tris.Cl, pH8.0, 10 mM MgCl$_2$, 20 mM KCl, and 1 mM β-mercaptoethanol). The mixtures were left for 5 minutes under temperature of 55° C. and separated by electrophoreting with 1% agarose gel. The gel was processed by 0.1×TAE buffer (4 mM Tris-Acetate, pH8.0, 0.1 mM EDTA) and electrophoreted with same buffer. Autoradiography after the electrophoration was shown in FIG. 5. p41–p46 complex bound to all types of DNA and shifted the band as the complex. It was not shown on the diagram but under this condition, p41, p46 alone did not show binding (band shifts were not found).

Example 9

Increase of Efficiency in DNA Synthesize by p46

Figure 6:
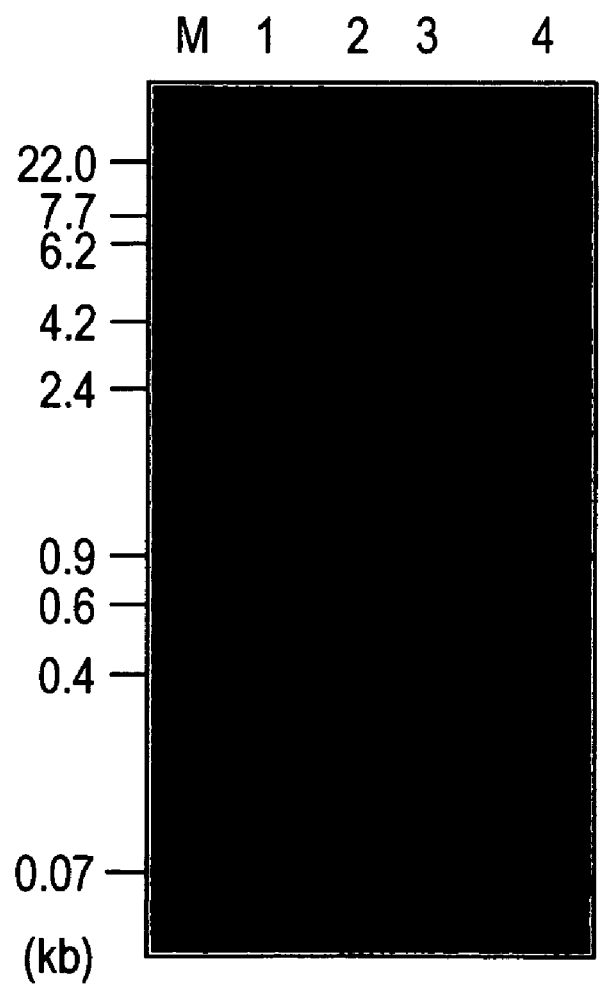
FIG. 6 shows a progress of DNA synthesis reaction by p46. DNA synthesis reaction (DNA primase assay) using p41 alone or p41–p46 complex was executed and studied by electrophoreting with alkaline agarose gel. Even under the condition that the product would not find by the reaction of the p41 alone (lane 1), extremely strong signal of the product was detected from complex (lane 2 and 3). When the quadruple reaction mixture of p41 alone was electrophoreted, a product was detected.

According to the method described in Example 5, effect of DNA synthesis of p41–p46 complex was compared with the case when the each protein synthesizes the DNA alone. Reacting condition was described as in Example 5 but as labelled compound, [α32p] dCTP was used instead of [α32p] dATP. The separated fraction by the cation exchange column chromatography described in Example 7 was used as sample of complex, but also in the case when the proteins that were purified alone respectively were added together at once was experimented. FIG. 6 shows an analysis of the reacted products by the electrophoration. When the reaction mixture of p41 alone (lane 1), or p41–p46 complex (lane 2), and purified complex (lane 3) were electrophoreted for the same quantity, it was very clear that extremely strong signal was detected from lane 2 and 3. p41 alone was difficult to find a signal (lane 1), but when it was electrophoreted for a quadruple, it became much easier to find (lane 4). Even if the p41 became easier to find, it still showed a weaker signal compared to products form the complex. Also, it was not shown on the diagram but p46 alone did not show any DNA synthesis activity.

Figure 7:
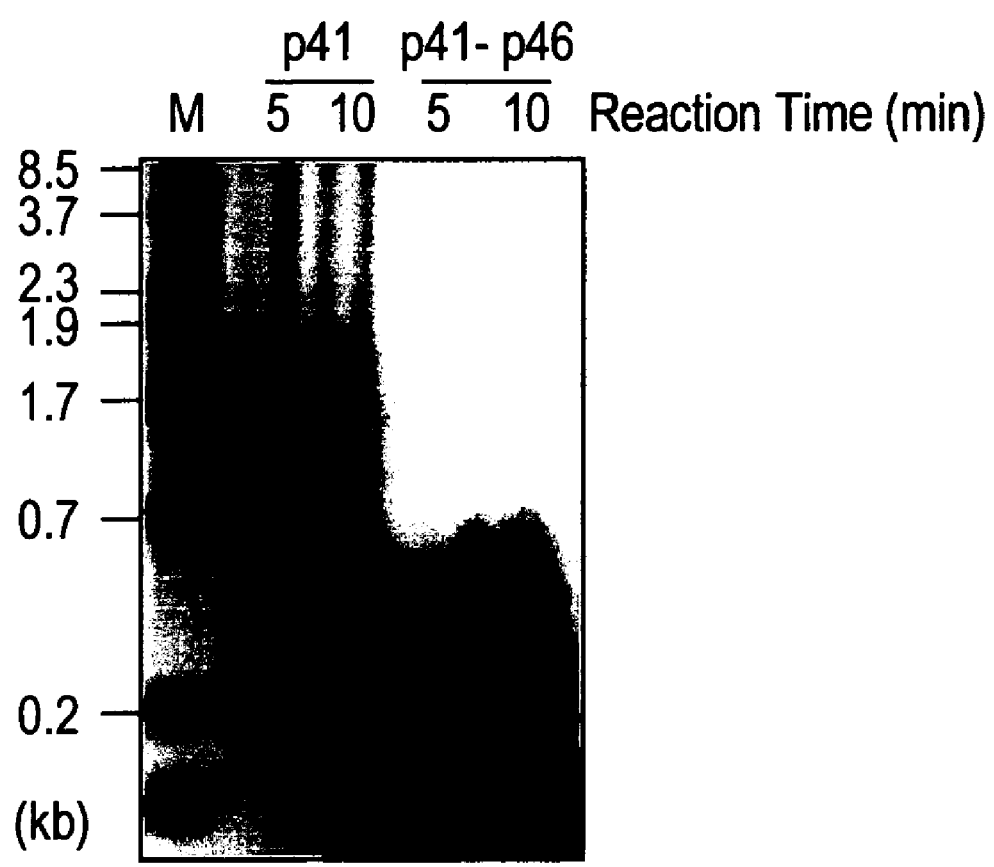
FIG. 7 shows progress of DNA synthesis reaction by p46. Using p41 alone or p41–p46 complex, DNA synthesis reaction (DNA polymerase assay) was executed. The reaction mixture was electrophoreted with alkaline agarose gel after 5 minutes and 10 minutes of reaction and studied. Compared to the reaction of p41 alone, complex had shorter chain but extremely strong signal is detected.

According to the method described in Example 6, effect of DNA synthesis of p41–p46 complex that depended on the primer was compared with the case when the each protein synthesized the DNA with alone. As FIG. 7 shows, compared with the reaction of p41 alone, the reaction of p41–p46 complex produced much more products even though the length of extending chain was short.

As described above, p46 enforces DNA synthesis activity of p41 that is dependent or independent to the primer by forming complex.

---

The invention claimed is:

1. An isolated polypeptide comprising the amino acid sequence set forth in SEQ ID NO:1.

2. A method of producing a polypeptide according to claim 1 comprising:
 a) obtaining a polynucleotide molecule that encodes a polypeptide having an amino acid sequence shown in SEQ ID NO:1;
 b) inserting the polynucleotide molecule into an expression vector;
 c) transforming a host cell with the expression vector;
 d) cultivating the transformant under conditions wherein the polypeptide encoded by the polynucleotide molecule is expressed; and
 e) isolating the polypeptide encoded by the polynucleotide molecule from the culture.

3. A method of producing a polypeptide according to claim 1 comprising:
 a) cultivating a host cell transformed with an expression vector comprising a polynucleotide molecule, wherein said polynucleotide molecule encodes a polypeptide comprising the amino acid sequence as set forth in SEQ ID NO:1, under conditions whereby the encoded polypeptide is expressed; and
 b) isolating the polypeptide expressed in a).

* * * * *